(12) United States Patent
Tsuneki et al.

(10) Patent No.: US 6,559,342 B1
(45) Date of Patent: May 6, 2003

(54) METHOD OF PRODUCING ALKANOLAMINES AND APPARATUS FOR PRODUCING SAME

(75) Inventors: Hideaki Tsuneki, Tokyo (JP); Masaru Kirishiki, Suita (JP); Yoshitaka Arita, Nishinomiya (JP); Yukihide Hashimoto, Takarazuka (JP); Tomoharu Oku, Suita (JP); Hisakazu Shindou, Suita (JP); Yoshiaki Urano, Kawasaki (JP); Fumiaki Morishita, Tokyo (JP)

(73) Assignee: Nippon Shokubai Co., Ltd., Osaka (JP)

( * ) Notice: Subject to any disclaimer, the term of this patent is extended or adjusted under 35 U.S.C. 154(b) by 0 days.

(21) Appl. No.: 09/717,593

(22) Filed: Nov. 21, 2000

(30) Foreign Application Priority Data

Nov. 26, 1999 (JP) .......................................... 11-336028
May 11, 2000 (JP) ........................................ 2000-138785
Jun. 5, 2000 (JP) ........................................ 2000-166882

(51) Int. Cl.$^7$ ............................................. C07C 213/04
(52) U.S. Cl. ...................................... 564/475; 564/477
(58) Field of Search ................................ 564/475, 477

(56) References Cited

FOREIGN PATENT DOCUMENTS

| EP | 0 652 207 A1 | 5/1995 | .......... C07C/213/04 |
| EP | 0 941 986 A2 | 9/1999 | .......... C07C/213/04 |

*Primary Examiner*—Brian Davis
(74) *Attorney, Agent, or Firm*—Fish & Richardson P.C.

(57) ABSTRACT

In producing alkanolamines by use of a microporous material as a catalyst, the difficulty in industrially performing the production because of the short lifetime of the catalyst is resolved. A process of regenerating the catalyst by removing an organic substance deposited on the catalyst by means of decomposing and/or extracting the substance is introduced, and thereby steady production is carried out substantially over the long term by switching the reaction and the regenerating processes.

11 Claims, 6 Drawing Sheets

METHOD OF PRODUCING ALKANOLAMINES AND APPARATUS FOR PRODUCING SAME

BACKGROUND OF THE INVENTION

1. Field of the Invention

The present invention relates to a method for producing an alkanolamine by the reaction of ammonia with an alkylene oxide by the use of a microporous material as a catalyst, and an apparatus thereof. Particularly The present invention relates to a method for selectively producing dialkanolamine and an apparatus thereof. More particularly, it relates to a method for producing an alkanolamine by combining the regenerating process of the deactivated catalyst and the process of allowing ammonia to react with an alkylene oxide, and the apparatus therefor.

2. Description of the Related Art

A method of producing ethanolamines by allowing ethylene oxide to react with aqueous ammonia (the concentration of ammonia: 20–40% by weight) is industrially adopted as a method of producing alkanolamines by amination of alkylene oxides with ammonia. In the method, three types of alkanolamines such as monoethanolamine, diethanolamine, and triethanolamine are produced. However, since the demand for the trietanolamine decreases, it is necessary that the production of trietanolamine be suppressed. For this reason, the reaction is typically carried out at a molar ratio of ammonia to ethylene oxides of about 3 to 5 by use of a large excess of ammonia, but the selectivity to trietanolamine is still 10–20% by weight or more.

On the other hand, an alkylene oxide hardly reacts with ammonia in the system where water does not exist. Accordingly, a catalyst is indispensable for such a reaction. For instance, homogeneous catalysts such as organic acids, inorganic acids, and ammonium salts; ion-exchange resins having a sulfonic acid group fixed therein, acid-activated clay catalysts, various zeolite catalysts, and rare-earth-element-carrying catalysts are proposed. However, the purpose of these catalysts is to highly selectively produce monoalkanolamines, and to produce dialkanolamines, the demand of which increases in recent years, is still insufficient.

A catalyst with a high selectivity to dialkanolamines can be produced by using a catalyst which is a microporous material having an effective pore size of 0.45–0.8 nm, or such a microporous material which was ion-exchanged and/or surface-treated.

In the case where dialkanolamines are required to be produced in a still higher selectivity by use of these catalysts, the dialkanolamine can be increasingly produced by separating the produced monoalkanolamine and then recycling part thereof to the reaction system.

SUMMARY OF THE INVENTION

When a microporous material is used as the catalyst, the activity of the catalyst may decrease at a comparatively short time. It has never been known so far that the reduction in the activity occurs in producing the alkanolamine. Because the catalyst is expensive, it should not be thrown away after one use, but it should be practically reused in some way. However, the specific apparatus and method for the reaction, which can be industrially advantageously used, have never been known yet.

We have vigorously studied for solving the above problems. As a result, we have found that the deactivated catalyst can be regenerated and have achieved this invention.

In addition, we have found that by alternately repeating a regenerating process of the deactivated catalyst and a process of allowing ammonia to react with an alkylene oxide, a desired alkanolamine can be produced while the regenerating process is being done and an apparatus therefor. We have completed the invention.

An object of the present invention is therefore to provide a method for regenerating the deactivated catalyst.

Another object of the present invention is to provide a method for producing an alkanolamine while the deactivated catalyst is being regenerated.

Still another object of the present invention is to provide an apparatus for producing an alkanolamine while the deactivated catalyst is being regenerated.

More specifically, the object of the present invention is attained by a method of producing an alkanolamine by alternately repeating a regenerating process of the deactivated catalyst and a process of allowing ammonia to react with an alkylene oxide, in producing the alkanolamine by allowing ammonia to react with the alkylene oxide by use of a microporous material as the catalyst.

Moreover, the object of the present invention is attained with an apparatus of the production of an alkanolamine by allowing ammonia to react with an alkylene oxide by use of a microporous material as the catalyst, comprising (a) multiple reactors, all of which have a regenerating unit, and (b) a switching valve which is used to perform the reaction of ammonia with an alkylene oxide in the remaining reactors while the regeneration is being done in at least one of the reactors.

The object of the present invention is attained by a method of regenerating a catalyst for producing an alkanolamine by reaction of ammonia with an alkylene oxide, wherein the catalyst is a microporous material catalyst, and ammonia is passed through the catalyst at 100–350° C.

Another object of the present invention is attained by a method of regenerating the catalyst for producing an alkanolamine by treating the catalyst with ozone in a gas phase, in regenerating the microporous material catalyst used for producing an alkanolamine by reaction of ammonia with an alkylene oxide.

In accordance with the present method, since a deactivated catalyst can be regenerated, it can be reused as the catalyst.

In accordance with the present apparatus, since multiple reactors are installed therein, an alkanolamine, particularly a monoalkanolamine and dialkanolamine can be selectively produced while the deactivated catalyst is being regenerated.

In accordance with the present method, since multiple reactors are installed therein and an alkanolamine can be produced while the deactivated catalyst is being regenerated, the production efficiency is high.

In accordance with the present method, since multiple reactors are installed therein, a monoalkanolamine and dialkanolamine can be selectively produced while the deactivated catalyst is being regenerated.

The above and other objects, features and advantages of the present invention will become clear from the following description of the preferred embodiments.

BRIEF DESCRIPTION OF THE DRAWINGS

The accompanying drawing incorporated in and forming a part of the specification, illustrates several aspects of the present invention, and together with the description serve to explain the principles of the invention. In the drawings.

DESCRIPTION OF THE PREFERRED EMBODIMENTS

Figure 1:
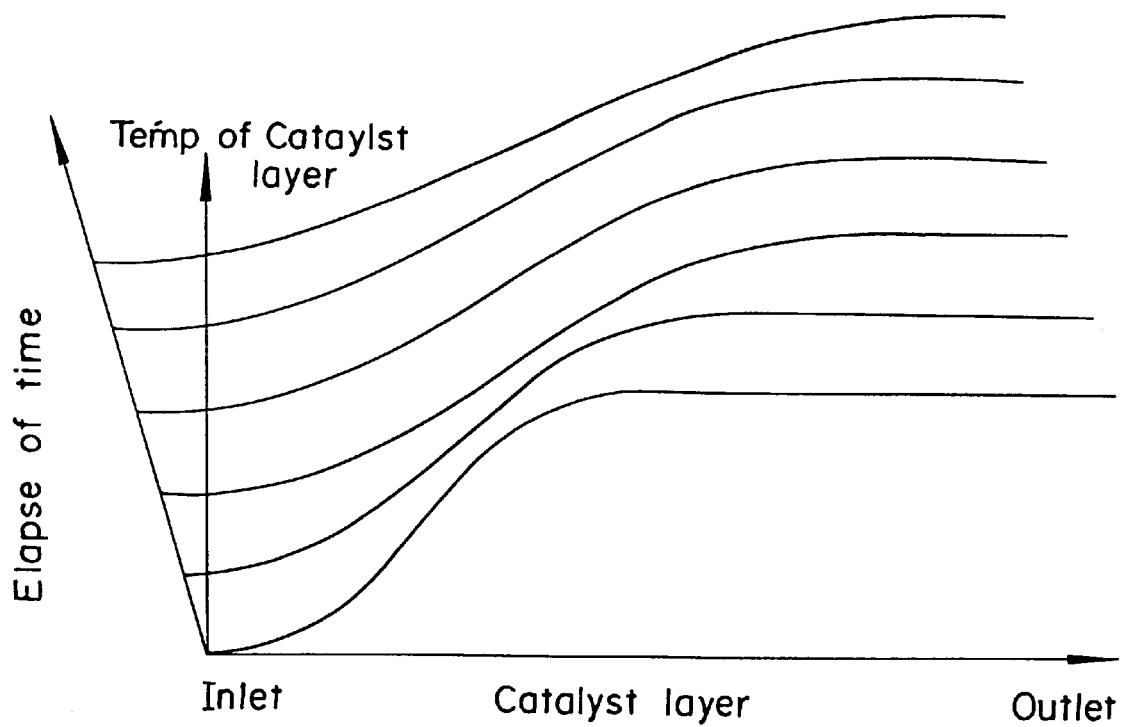
FIG. 1 is a schematic diagram showing an example of the change of temperature distribution with time within the reactor in the method of the present invention.

The term "regeneration" as used herein means that by decomposing and/or extracting, and thereby removing the organic substance attached or deposited on or within the inorganic solid catalyst, the catalyst is allowed to recover the activity that it had had before the organic substance was attached or deposited on or within the catalyst. The degree of recovering the activity may be typically 80% or more of the activity that the fresh catalyst has, preferably 90% or more, more preferably 95% or more.

Any of the catalysts can be used as long as the catalyst, which is used in the present invention, is a microporous material catalyst used to produce an alkanolamine, particularly a dialkanolamine from an alkylene oxide and ammonia in a liquid phase while depressing the formation of a trialkanolamine. Examples of the microporous material catalysts include a catalyst typically having an effective pore size of 0.45–0.8 nm or a catalyst that is a microporous material that was ion-exchanged and/or surface-treated.

The microporous material is a crystal having pores of an almost uniform diameter of a molecular size. Examples of the material include types of ① metallosilicate and ② aluminophosphate. As ① metallosilicate type, aluminosilicate which is the metallosilicate having aluminum as its metal is known as so-called zeolite, and as metals forming the other metallosilicates, Fe, Ga, B, Co, Ni, Cr, Sc, Ge, Ti, and Zn are known. As ② aluminophosphate type, aluminophosphate (ALPO), metalloaluminophosphate (MAPO), and silicoaluminophosphate (SAPO) are known.

In addition, with regard to the types of crystal structure (namely, the structure of pore) of metallosilicate, MFI, MEL, MOR, BOG, TON, MTW, ATO, AFR, and BEA, etc. (these are shown using the frame work topology code of the International Society of Zeolite for showing the crystal structure) are cited. MFI or MEL is more preferable with respect to the selectivity of dialkanolamines.

There is ZSM-5 known as a synthesized-high-silica-type zeolite having the MFI structure. In addition, there is ZSM-11 known similarly as a synthesized-high-silica-type zeolite having the MEL structure. MFI and MEL look like well each other in the structure, and ZSM-5 and ZSM-11 may have both crystalline structures because intergrowth occurred. However, both zeolites can be used in the present invention.

Since the reaction of alkylene oxides with ammonia or amine takes place primarily within the pore, the effective pore size of the microporous material mentioned above may be typically in the range of 0.45 to 0.8 nm, more preferably 0.5 to 0.7 nm in order to heighten the selectivity. Preferable examples of such a microporous material include MFI, MEL, MOR, TON, MTW, ATO, AFR, BEA or the like. MFI and MEL are more preferable among them with respect to the selectivity to dialkanolamines.

Because a X type or Y type zeolite which have large cavities therein can produce a big molecule within the cavities, it is almost impossible to show the expected shape-selectivity by the pore diameter at the inlet and outlet of the pore. Moreover, it is preferable to inactivate the outer surface of the primary particles of the crystals, because the shape-selectivity is not expected in the reaction outside the pore. Examples of the inactivation method include steaming treatment at a high temperature, silicon-tetrachloride treatment, and alkoxysilane treatment.

The specific methods of producing metallosilicate are as follows: a metallosilicate is produced by a so-called hydrothermal synthesis method in which a silica source, a metallic source, and a structure-directing agent are typically suspended in water, and then the resulting mixture is heated in an autoclave; or by a so-called dry gel method in which a gel that was produced by concentrating and evaporating to dryness a silica source, a metallic source, and a structure-directing agent, is contacted with steam in an autoclave. Moreover, ALPO, MAPO, and SAPO can be similarly produced by the hydrothermal synthesis except that phosphoric acid is used. In addition, commercially available ZSM-5 and BEA can be used. The ion exchange sites of the microporous material produced by the hydrothermal synthesis typically contain alkali metal ions as a pair cation. Because the activity of microporous materials is often weak as it is, the alkali metal ions are ion-exchanged once with $NH_4^+$ ions, and then the material is calcined at a high temperature to thereby be changed to the proton type. In addition, after the ion exchange is performed with $NH4^+$ ions once, the ions can be exchanged by multivalent cations again. The ion exchange with the rare earth element is preferable because the ion exchange improves often the activity and the selectivity.

Molding or forming a catalyst is preferable in industrial use. The shape of the catalyst is not particularly restricted, but includes for example a spherical, cylindrical, and hollow-cylindrical shape. A microporous material such as metallosilicate consists of very fine crystals, and its molding properties are very poor by themselves. Therefore, it is preferable to use a molding auxiliary or a binder to mold the material. In that case, various oxide sols such as silica sol, alumina sol, and zirconia sol and clay or mineral matters are used as the molding auxiliary and binder. The clay minerals such as smectite group and kaolin are preferable with respect to the improvement in the molding properties. In order not to damage the activity and selectivity that the catalyst inherently has, it is preferable to use smectite clay having the activity in the reaction of ammonia with an alkylene oxide by itself, particularly monmorillonite among them. Using such a molding auxiliary makes it possible to mold the material smoothly, and then does not impair the inherent properties of the catalyst used in the present invention because the molding auxiliary has the activity and selectivity by itself. When the molding auxiliary is used, the amount of the auxiliary is not particularly restricted as long as the catalytic material can be molded. An amount of the auxiliary may be typically 50 parts by weight or less with respect to 100 parts by weight of the microporous material, more preferably 40 parts by weight or less. In addition, in the catalyst with a certain size by being molded, it is preferable to increase the volume of pores, in order to prevent the reduction in the activity and selectivity caused by the influence of diffusion within the catalyst. It is preferable therefore to increase the volume of pores by adding a pore-forming agent to the material, then molding the material, and removing the agent by calcination treatment. Examples of the pore-forming agent include various ammonium salts such as ammonium nitrate and ammonium acetate; organic compounds such as oxalic acid and urea; and water-insoluble organic compounds such as a variety of polymers and fibers. The water-insoluble compound can be preferably used because of its efficiency of pore-formation and excellent moldability. Examples of the water-insoluble compound include any material, as long as it has moisture absorption to some extent, is a fine powder, and can be calcination-removed by a high-temperature treatment at a temperature of several hundred degrees. Crystalline cellulose is especially used because of its excellent handlingability. As the crystalline cellulose, the powders obtained by pulverizing filter paper or pulp can be used. In using the organic material such as the crystalline cellulose as the pore-forming agent, the material cannot be decomposed by mere heat treatment. It is removed by calcining it in a gas such as an oxygen-containing nitrogen, helium, or carbon dioxide (air is convenient).

It is possible to produce a molded metallosilicate by supporting on a molded silica a metal source such as aluminum, an alkali, and a structure-directing agent, and then contacting the silica with steam in an autoclave.

It is preferable that ammonia used as the raw material in the present invention does not substantially contain water. This is because a great amount of water contained in the ammonia may affect negatively the activity and the regeneration of the catalyst. Therefore, the amount of water is preferably 1% or less, more preferably 0.1% or less with respect to the weight of the ammonia.

The alkylene oxide used as the raw material in the present invention is preferably an alkylene oxide represented by the following formula (1):

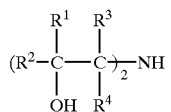

(1)

wherein $R^1$, $R^2$, $R^3$, and $R^4$ each independently represent a hydrogen atom, a methyl group or an ethyl group. Examples of the alkylene oxide include alkylene oxides having 2–4 carbon atoms such as ethylene oxide, and propylene oxide, etc. The corresponding alkanolamines are obtained from these raw materials.

Examples of the alkanolamine include a monoethanolamine represented by the following formula (2):

(2)

wherein $R^1$, $R^2$, $R^3$, and $R^4$ are the same as in the formula (1), and diethanolamines, trietanolamines, and propanolamines represented by the following formula (3):

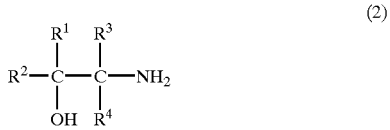

(3)

wherein $R^1$, $R^2$, $R^3$, and $R^4$ are the same as in the formula (1).

A well-known method and apparatus can be used for the reaction. The reaction pressure must be typically maintained higher than the vapor pressure of the reaction mixture at the highest temperature within the reactor because the reaction must be performed under solution conditions. In the case the removal of the reaction heat is difficult because of the high concentration of the alkylene oxide, part of the ammonia is vaporized to generate an evaporation latent heat and using the evaporation latent heat, the reaction heat can be removed. In this case, it is preferable to reduce the reaction pressure lower than the vapor pressure of the reaction solution at the highest temperature within the reaction system.

Producing the alkanolamines can be typically performed in the temperature range of 40–300° C., preferably 80–200° C. The operating pressure may be in the range of 1–20 MPa. The liquid hourly space velocity (LHSV) is not restricted under the above-described conditions, but a condition of 0.1 $hr^{-1}$ or more may be typically used. LHSV is represented by the following formula:

$$LHSV=A1/B1$$

wherein
 A1=the volume of the liquid raw material which passes the reactor per hour ($cm^3$/hr),
 B1=the volume of catalysts within the reactor ($cm^3$).

The dialkanolamine can be produced more effectively without recycling the monoalkanolamine as long as the microporous material is used as the catalyst. The production of the dialkanolamine can be increased by recycling part of the produced monoalkanolamine to the reactor when the concentration of the alkylene oxide at the inlet of the reactor has a limiting factor, for instance, in the case an adiabatic one-step reaction is performed, or when it is not necessary to produce monoalkanolamines so much.

In addition, when carrying out the reaction by increasing the ratio of an alkyleneoxide to ammonia (namely, by increasing the concentration of the alkylene oxide) in order to increase the production of dialkanolamines, the reaction mixture coming out from the reactor is cooled once; the needed alkylene oxide is added thereto, and then the reaction mixture is fed to the next reactor to perform the reaction; because the temperature increase of the reaction mixture becomes too high in one-step reaction.

When the microporous material catalyst is used in the reaction for a long period, the decrease in activity thereof which seems to be caused by the deposition of the organic substance on or within the catalyst is observed, and the yield of the desired product, alkanolamine decreases.

Introducing a rinsing process prior to the regenerating process is preferable. The rinsing process is a process where the alkanolamines within the system is flushed outward from the reactor, and the alkanolamines absorbed within the catalyst is desorbed and removed. Liquid ammonia is used for rinsing. The rinsing conditions with liquid ammonia are not particularly restricted, but a fairly high temperature is preferable to raise the rinsing efficiency. More specifically, rinsing may be performed typically at 50° C. or more, preferably 60° C. or more, and more preferably in the range of 80 to 150° C. If a time is used enough to desorb the alkanolamine from the catalyst, the amount of the liquid ammonia used for rinsing is not particularly restricted. However the volume is typically two times or more of the apparent volume of the catalyst to be regenerated, preferably in the range of 10–100 times. According to circumstances, the rinsing with water or other solvents can be additionally performed. Particularly, when the aqueous solution of oxidizing agent is used to regenerate the catalyst, the rinsing with water is preferable. When the regeneration is carried in a vapor phase, additional replacement with an inert gas is preferable.

Deactivated catalysts have the deposited organic substance, and the deposition seems to be the reason for the reduction in the activity. In order to treat the deactivated catalyst, the following methods may be cited:

(1) The deactivated catalyst is treated with ammonia at a predetermined temperature.
(2) The deactivated catalyst is treated with an ozone-containing gas in a gas phase.
(3) The deposited organic substance is oxidized and decomposed in the presence of an oxygen-containing gas (air or the gas that is the air diluted with an inert gas such as nitrogen is preferable.) at a high temperature (300° C. or more, preferably 400° C. or more, more preferably 500° C. or more, but the upper limit is 700° C. or less). The deposited organic substance is treated, if necessary, in a stream of an oxygen-containing gas, at a high temperature. If a time is used enough to remove the adhering organic substance from the catalyst, the amount of the oxygen-containing gas is not particularly restricted. The volume may be typically 100 times or more of the apparent one of the catalyst to be regenerated, preferably in the range of 200 to 1000 times.
(4) The deposited organic substance is oxidized and decomposed with an oxidizing agent such as hydrogen peroxide at a comparatively low temperature.
(5) The deposited organic substance is extracted with a solvent such as water or liquid ammonia.
(6) It is possible to decompose the deposited organic substance at a high temperature by using the acidic properties, which the catalyst inherently has, and to combine the methods of (1)–(6) properly. It can be said that the regenerating treatment is decomposition-removal and/or extraction-removal treatment for the remaining organic substance.

Regenerated catalysts can be used again as a catalyst.

In alternately repeating a regenerating process for regenerating the deactivated catalyst and a process where ammonia reacts with alkylene oxides, both processes can be performed within a single reactor. However, it is preferable to use multiple reactors to perform the reaction process continuously, because the reaction stops during the regenerating process in a single reactor. Accordingly, it is preferable to provide multiple reactors and a switching valve to continuously perform the reaction. It should design, while a part of the reactors are being regenerated, a flow path to be able to continue the reaction in the remaining reactors and continue the reaction by switching the reactors without stopping the reaction.

Suitable examples of continuous reactions with the reactor include the following processes:

Multiple insulation type reactors are used, and while the regeneration is performed in at least one of the reactors, ammonia is reacted with alkylene oxides in the remaining reactor; and The reaction is carried out by connecting in series part or all of those reactors used in the reaction process, the reactor including the most deactivated catalyst is successively separated from the reaction process, and then switched to the regenerating process, and the regenerated reactor is added to the reaction process.

In order to produce such alkanolamines, it is possible to use an apparatus which is used for producing alkanolamines by the reaction of ammonia with alkylene oxides by use of a microporous material as a catalyst, comprising (a) multiple reactors, all of which have a regenerating unit, and (b) a switching valve which is used to perform the reaction of ammonia with alkylene oxides in the remaining reactor while the regeneration is being done in at least one of the reactors. Examples of the switching valves include an on-off and three-way valves which change the flow of fluid. In addition, the regenerating unit includes a pump that conveys an oxygen-containing gas, an oxidizing agent, and solvent for regenerating, an ozone generator and the like.

The switching valve is installed each in the raw-material-supply conduit and the product-conveying conduit, and a multiple switching valves may be installed. It is preferable in the above-mentioned apparatus that (a) the apparatus has a switching valve and a flow path which is used to connect a part or all of the reactors in series, and that (b) any of the reactors that are connected in series can be positioned at the head of the line. In order to attain such an arrangement, for instance, it is required that one switching valve is installed each in the raw-material-supply conduit and the product-conveying conduit of each the reactor; a pipe with a switching valve therein is connected from between the reactor of which order is n (n is 3 or more) and the switching valve at its product-conveying conduit to between the reactor of which order is (n+1) and the switching valve at its raw-material-supply conduit; and a pipe with a switching valve therein is connected from between the last reactor and the switching valve at its product-conveying conduit to between the first reactor and the switching valve at its raw-material-supply conduit. Multiple switching valves may be installed in those pipes when each the position of the reactor is far from each other.

Now, the present invention will be described in detail with reference to the drawings.

FIG. 1 is a schematic diagram showing one example of the temperature distribution changes with time within the reactor that shows the reduction degrees in catalytic activity. As shown in FIG. 1, there is sufficiently high activity at the first stage of the reaction by use of an insulation type reactor, so that the reaction is completed at the inlet of the catalytic layer and the alkylene oxide, which is the raw material, had been already consumed near the center or the outlet of the catalytic layer, thereby the further increase in the temperature of the catalytic layer is not shown. As the reaction progressed, the activity gradually reduces from the inlet of the catalytic layer to lower the rate of reaction and to decrease the heat, the high temperature part in the temperature profile of the catalytic layer slide to the back of the catalytic layer, and finally the alkylene oxide is not sufficiently converted.

The larger amount of the catalyst is filled, the longer time the reactor can continuously be driven (=lifetime). On the other hand, because the liquid hourly space velocity (LHSV) is very small, a large amount of catalyst and a very great reactor are needed. The conditions are difficult to industrially adopt.

The means for switching the reaction process and the regenerating process includes using a single reactor and using multiple reactors. When the lifetime of the catalyst is comparatively long and the time required for regenerating process is short, a single reactor is used and the deactivated catalyst is regenerated when the reaction stops. However, there is a tendency that the reactor becomes large in this case, and the running is accompanied by the stop of the reaction, with the result that the problems remain industrially.

Multiple reactors is preferably used so as to reduce the volume of the reactor (the necessary amount of the catalyst), and operate the reactor without stopping the reaction.

Figure 2A:
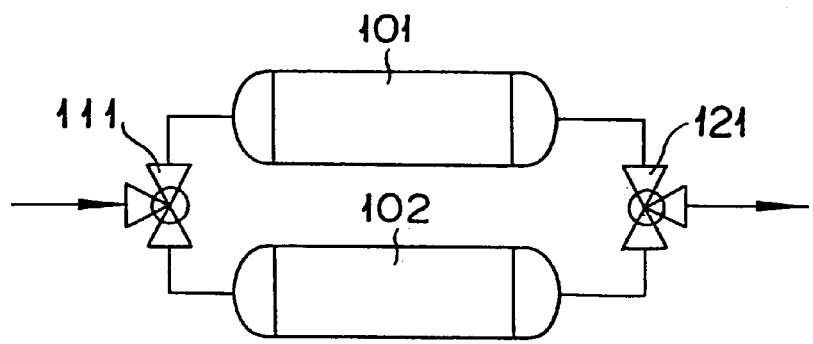
FIGS. 2A–B are schematic diagrams of a parallel type reaction apparatus in the present method.
Figure 2B:
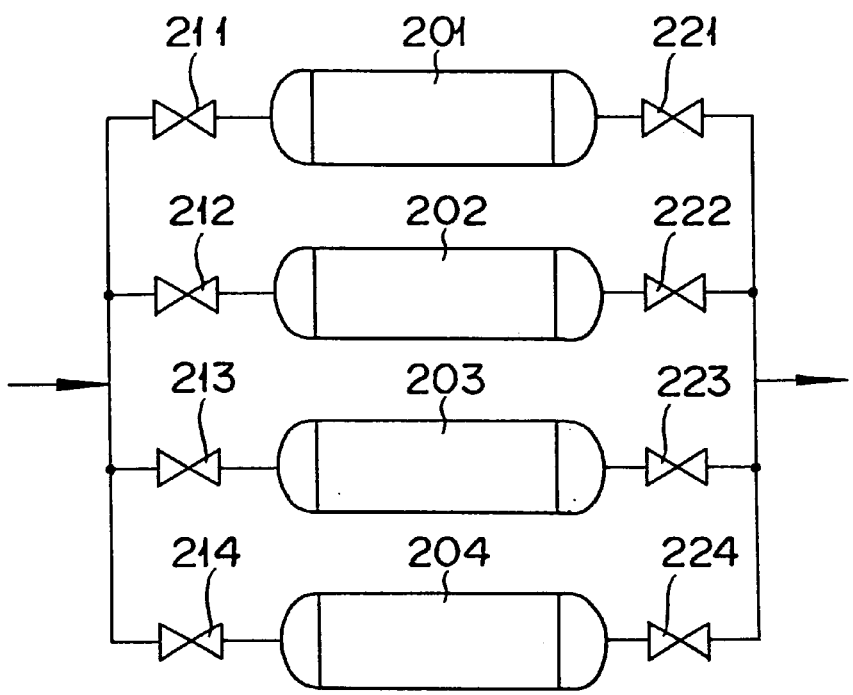

FIG. 2 is schematic diagrams of the reaction apparatus in which reactors are arranged in parallel in the present method. FIG. 2A shows an example of two reactors, and FIG. 2B shows an example of four. In FIG. 2A, the reactor 101 is in the regeneration process, and a steady and continuous running is possible if the reaction is processed with the other reactor 102. The process is switched by controlling the switching valve 111 installed at the raw-material-supply conduit and switching valve 121 installed at the product-conveying conduit. It is also possible to automatically operate each switching valves.

When the time required for the regenerating process is almost equal to the lifetime of the catalyst, two reactors is sufficiently used. However, when the balance is bad, for instance, if the regeneration requires 100 hrs and the lifetime is 300 hrs, the reactor for the regeneration is not used for 200 hrs after the regenerating process was ended. In such a case, as shown in FIG. 2B, three or more reactors (four reactors in this example) are used and, when the reactor where the reaction was done for 300 hrs one by one to the regenerating process, the reactors are effectively used. More specifically, the operation is as follows: when a reactor 201 is switched to the regenerating process, a reactor 202 where the regeneration is just ended has a performed-reaction time of 0 hrs, a reactor 203 has a performed-reaction time of 100 hrs, and a reactor 204 has a performed-reaction time of 200 hrs. When the regeneration of the reactor 201 is ended after 100 hrs later, the reactor 202 has a performed-reaction time of 100 hrs, the reactor 203 has a performed-reaction time of 200 hrs, and the reactor 204 has a performed-reaction time of 300 hrs, and then the reactor 204 which reached the lifetime is switched to the regenerating process. The process is switched by controlling each on-off valves 211, 212, 213, and 214 installed at the raw-material-supply conduit of the reactor and each on-off valves 221, 222, 223, 224 installed at the product-conveying conduit. Of course, it is also possible to automatically control each the on-off valves (the same with the on-off valves thereafter).

When lifetime of the catalyst is remarkably short, it is also possible to apply multiple reactors to the regenerating process oppositely.

As shown in FIG. 1, the activity of the catalytic layer tends to decrease from the inlet part thereof. In the method of connecting the reactors in parallel, as shown in FIG. 2, the reduction level of the catalytic activity depends on the reactor, and the raw material is almost consumed an inlet part of the catalytic layer, so that it is impossible to effectively use the latter half of the reactor immediately after the regeneration. The reaction can be carried out most efficiently if the reactors are connected in series, and the flow paths and switching valves are arranged such that any reactor can be positioned at the head of the row.

Figure 3:
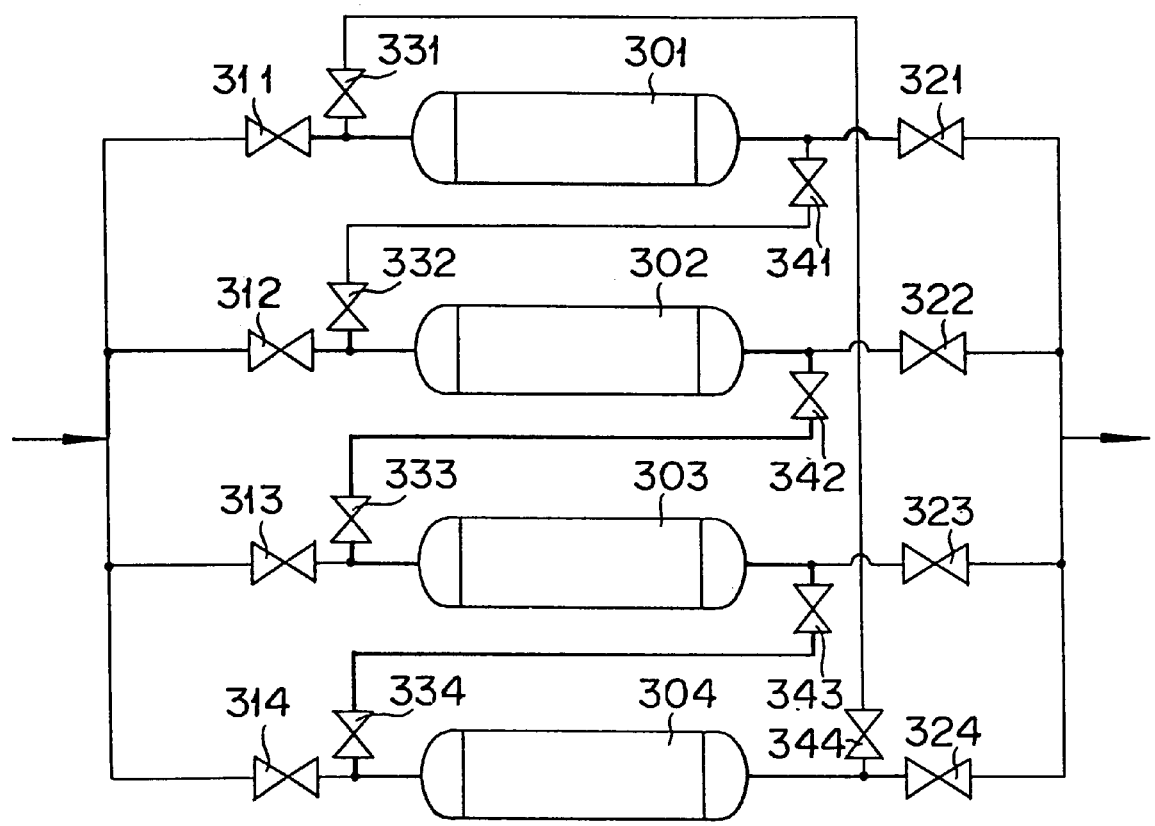
FIG. 3 is a schematic diagram of an in-line type reaction apparatus in the present method.

FIG. 3 is a schematic diagram showing an example of the reaction apparatus having the reactors arranged in series in the present method. In FIG. 3, the route indicated by the thick line is a flow path for the raw material and the product, and reactors 302, 303, and 304 each are connected in series. In the flow path shown in FIG. 3, on-off valves 312, 342, 333, 343, 334, and 324 through which the thick line passes each are opened, and the other valves are closed. A reactor 301 is in the regenerating process. When the regeneration of the reactor 301 was ended, a reactor 302 in which the reduction in activity of the catalyst most advanced is switched to the regenerating process, a reactor 303 is arranged at the head to similarly be connected with reactors 304 and 301 in series, to perform the reaction. The process is switched by using on-off valves 311–314, 321–324, 331–334, and 341–344. After the process was switched, the reactor 303 is arranged at the head of the series, and the reactor 301 in which the regeneration was ended is arranged at the end of the row. For instance, the process is switched by the following procedures:

① First, the flow path of the reaction is secured for the reactor 301 in which the regeneration was ended. The switching valves 311 and 341 are closed, and the switching valves 321 and 331 are opened.

② The switching valve 344 is opened, at the same time the switching valve 324 is closed, and then the fluid is fed into the reactor 301.

③ The switching valve 313 is opened, at the same time the switching valves 312, 333, and 342 are closed, and then the reactor 303 is arranged at the head.

④ The reactor 302 which is far from the route is subjected to the regenerating process.

Figure 4:
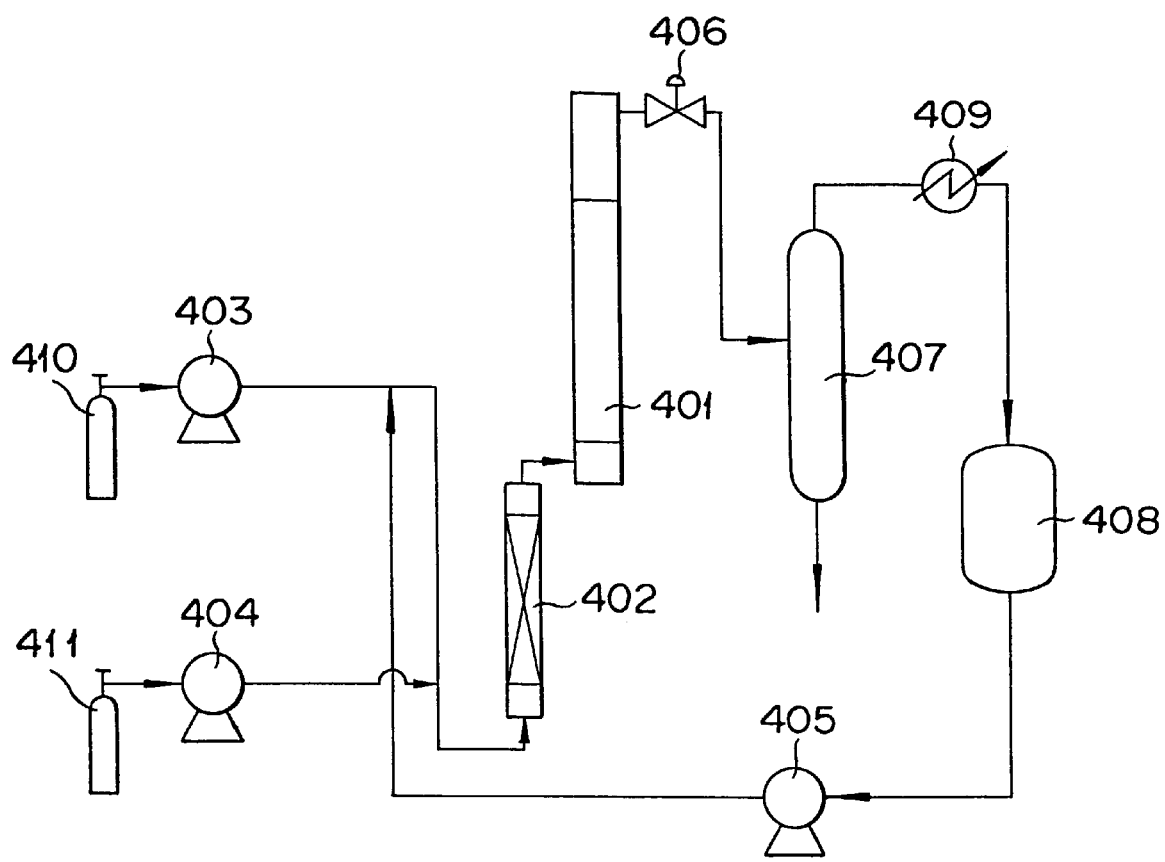
FIG. 4 is a drawing showing an example of a reaction apparatus in the case where a single reactor is used in the present method.

FIG. 4 is a drawing showing an example of the reaction apparatus in which a reactor is used in the present method. In FIG. 4, ethylene oxide, which is an alkylene oxide, is fed in the predetermined amount from an ethylene oxide raw material tank 411 via a high-pressure pump 404 to a pre-heater 402, and at the same time ammonia is fed in the predetermined amount from an ammonia raw material tank 410 via a high-pressure pump 403 to the pre-heater 402. The preheated raw material mixture is fed to a reactor 401 in which the catalyst is filled, while adjusting the pressure with a pressure control valve 406. The produced ethanol amines are collected in an ammonia flash tower 407 as a bottom liquid, and the unreacted ammonia is distilled off from the tower top and then condensed in a heat exchanger 409 to recover the ammonia in an ammonia tank 408. The collected ammonia is reused as the raw material via a high-pressure pump 405. When the catalytic activity decreased, the reaction is stopped, and then the catalyst is regenerated.

Methods of regenerating the deactivated catalyst, such as ammonia rinsing and using ozone in a gas phase will be described.

Catalyst Regeneration by Rinsing with Ammonia

In observing the deactivated catalyst, the catalyst does not discolor so much and has the deposited organic substance therein, but the phenomenon is not a so-called coking which is often seen in the reduction in activity of catalysts. When the coking occurred, the catalyst becomes black, and the organic substance becomes a carbon-like deposit. Such a substance can be removed only by oxidation at a high temperature. However, the reduction in activity of the catalyst in this reaction is not caused by coking, so that the catalyst can be regenerated by passing through the catalyst ammonia in liquid phase for example at a temperature range of 100 to 350° C. to decompose or extract the deposited organic substance.

The processing temperature may be in the range of 100–350° C., preferably 120–330° C., more preferably 140–300° C. If the temperature falls below 100° C., the efficiency of the decomposition and/or the extraction becomes reduced, and the catalyst cannot be sufficiently regenerated. Conversely, if the temperature exceeds 350° C., the coking of organic substances and the decomposition of the solvent happen to occur, as well as the costs for the reactors increase due to the design enduring a high temperature.

The pressure of regenerating treatment may be in the range of 1 to 30 MPa, preferably 1 to 25 MPa, and more preferably 1 to 20 MPa. If the pressure falls below 1 MPa, the regeneration cannot be sufficiently performed. Conversely, if it exceeds 30 MPa, the reactor costs will increase.

In the present regenerating method, it is also possible to withdraw the catalyst from the reactor once to treat it, but the operation becomes complex. Therefore, the catalyst is industrially advantageously processed while filled in the reactor. In this case, ammonia is fed to the catalyst-packed bed. The amount of ammonia to be used is not restricted as long as it is enough to remove the decomposition product in the ammonia, but it may be in the range of 0.01 to 50 $hr^{-1}$ (LHSV).

The time of the processing is necessary to recover the catalytic activity sufficiently. It may be in the range of 1 to 500 hrs depending on the processing temperature.

Figure 5:
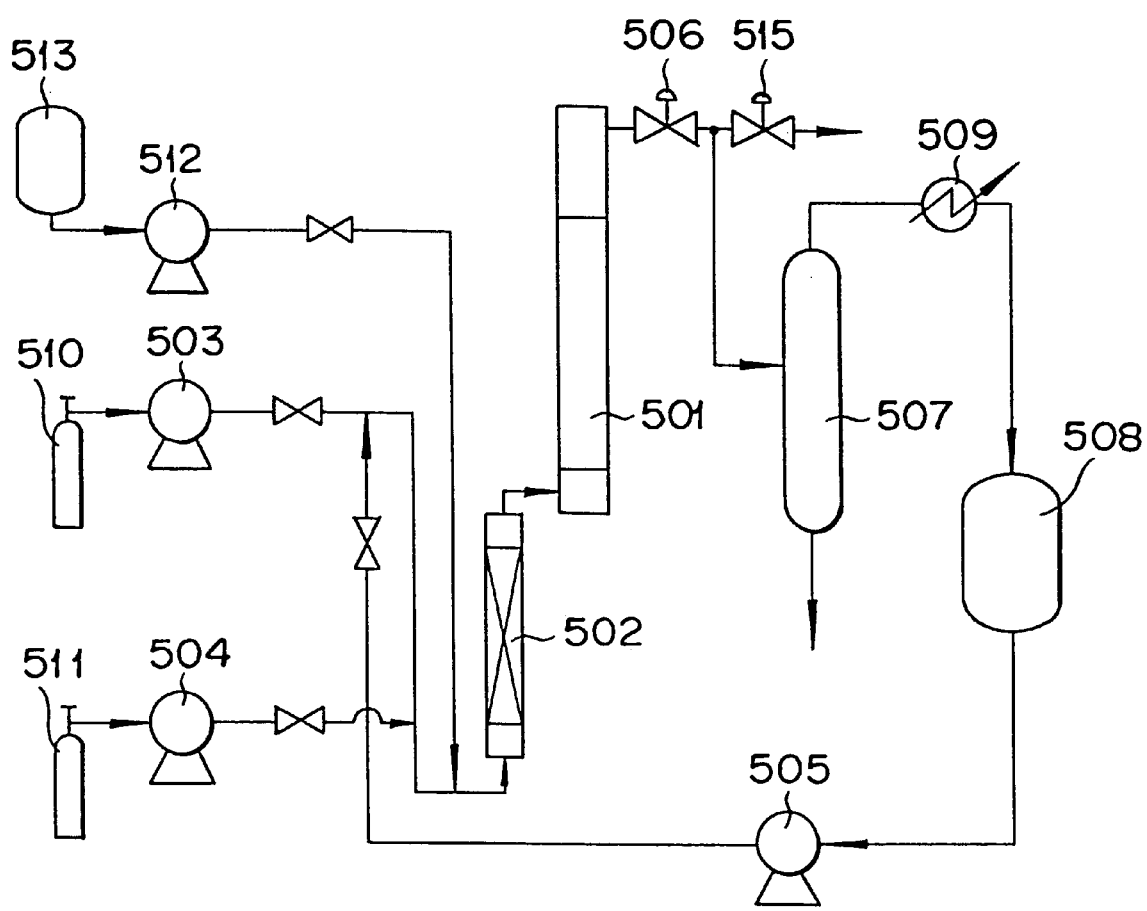
FIG. 5 is a schematic diagram of the reaction apparatus that was used in Example II.

A method of regenerating the catalyst according to the present invention will be described with reference to the drawing. FIG. 5 is a flowchart explaining a process of producing alkanolamines and a process of regenerating the deactivated catalyst. The process of producing alkanolamines will be first explained. In FIG. 5, ethylene oxide, which is one of alkylene oxides as a raw material, is fed in a predetermined amount from a tank for ethylene oxide 511 via a high-pressure pump 504 to a pre-heater 502, and at the same time, ammonia is fed in a predetermined amount from a tank for ammonia 510 via a high-pressure pump 503 to the pre-heater 502. The preheated raw material mixture is fed to a reactor 501 in which the catalyst was filled, while adjusting the pressure by a pressure control valve 506, to carry out the reaction and thereby produce ethanolamines. The produced ethanolamines are introduced to an ammonia-flash tower or column, and collected as a bottom liquid, and the unreacted ammonia is distilled off from the tower top and condensed in a heat exchanger 509, to thereby store the ammonia in an ammonia tank 508. The collected ammonia is reused as the raw material via a high-pressure pump 505.

The process of regenerating the catalyst will be described. When the reaction was ended, liquid ammonia is pre-heated if necessary, used to rinse the deactivated catalyst, and then discharged through an outlet valve 515 from the system. Then, a solvent for the regeneration is fed via a high-pressure pump 512 from a solvent tank 513 to the pre-heater 502. The solvent for regenerating is preheated, introduced into the reactor 501 to treat the catalyst, and then discharged through the outlet valve 515. The withdrawn solvent is measured with an analyzer such as a gas chromatograph to found the amount of high-boiling-point organic substances such as trialkanolamines. The degree of regeneration can be determined easily and promptly without discharging the catalyst from the reactor.

Moreover, when ammonia is used as a solvent, the ammonia used for the regeneration can be reused for the reaction.

Accordingly, the deactivated catalyst can be easily regenerated by passing ammonia through the catalyst in the range of 100 to 350° C. to remove the deposited organic substance by decomposition and extraction processes. Moreover, the solvent used is ammonia, which is the raw materials. Thus, it makes it possible to begin the production of the desired product readily after regeneration. In addition to the above, the regenerating method has an advantage in its capability to treat the deactivated catalyst for regeneration in the reactor, and thereby simplifies the process. Catalyst regeneration by use of vapor-phase ozone As a result of analysis of the deactivated catalyst, the cause seems to be the deposition of the organic substance on or within the catalyst. The carbon content in the deactivated catalyst is typically in the range of 0.5 to 15% by weight based on the weight of the catalyst.

Thus, it is required to reuse the regenerated catalyst after regenerating the deactivated catalyst in some way. In the conventionally regenerating method using a molecular-oxygen-containing gas, a combustion treatment at a high temperature such as at 400° C. or more, preferably 500° C. is required. In the case a large amount of organic substance existing on the catalyst is burned and removed with a molecular-oxygen-containing gas, the temperature of the catalyst during the regeneration rises extremely because of an extremely high calorific value. As a result, such a microporous-material catalyst receives thermal structural-destruction, the catalytic activity is irreversibly deteriorated, and thereby the catalyst cannot be regenerated.

In particular, it is necessary to design a reactor enduring to a temperature as much as 300–400° C. higher than the reaction temperature when the catalyst is regenerated within the reactor. Considering that the reaction is carried out at a high pressure of about 10 MPa, it is very difficult to use such a reactor.

Such a problem does not occur when the catalyst is discharged from the reactor and then treated. However, installation of a separate catalyst-regenerator is required as well as very complex operations such as discharging, regenerating, and re-packing the catalyst are required. Consequently, the method is practically difficult.

In this method, it is preferable to use ozone in a gas phase as an oxidizing agent in order to regenerate the catalyst under a mild condition. The use of the ozone having a strong oxidizing power makes it possible to lower the regeneration temperature and prevent the thermal deterioration of the catalyst during the regeneration. That is, when water in a liquid phase is used, for instance, catalytic active components are eluted therein, or the catalytic structure is irreversibly destroyed because of hydration. In addition, when the water remaining in the regenerating process negatively affects the reaction, the costs for drying are further needed because of the full drying after the regeneration. However, using ozone in a gas phase resolves these problems.

As the ozone-containing gas (referred to also as regenerating gas) used in the present invention, a ozone-containing gas that is generated by any method such as air-discharge method, discharge method in a gas containing a high concentration of oxygen, or water-electrolysis method, can be used as it is. However, the gas is preferably diluted as required with an inert gas such as nitrogen or a combustion gas from the outlet of the catalytic layer, from the viewpoint that the concentration of ozone in the gas is simply controlled.

The pressure during the regeneration is not particularly restricted, may be in a range from atmospheric pressure to 5000 hPa, preferably from atmospheric pressure to 3000 hPa.

The concentration of ozone in the ozone-containing gas for regeneration which is fed to the catalytic layer is not particularly restricted, when considering the treating time, it may be, based on the total amount of the ozone-containing gas, in the range of 0.05 to 5% by volume preferably in the range of 0.1 to 3% by volume. The gas other than ozone in the ozone-containing gas may contain nitrogen and oxygen. Each the content is not restricted, but the ratio by volume of nitrogen and oxygen is 1–1000:1, preferably 2–500:1.

The amount of the ozone-containing gas passing through the catalytic layer is not restricted as long as it can remove or rinse the organic substance deposited on the catalyst. It may be typically in the range of 50 to 10000 hr$^{-1}$, preferably 80 to 8000 hr$^{-1}$ (GHSV). Here, the term GHSV is shown by the following formula:

$$GHSV=A2/B2$$

wherein
A2=the volume of a gaseous raw material passing the reactor per hour (cm$^3$/hr),
B2=the volume (cm$^3$) of the catalyst in the reactor.

When the conversion of the ozone is low at the outlet of the catalytic layer, a part of the regenerating gas is preferably recycled to the inlet, considering that the volume of the regenerating gas is reduced.

The regenerating time may be in the range of 1 to 500 hrs, preferably 2 to 300 hrs, depending on the processing temperature, the ozone concentration, the amount of deposited organic substances, and the volume of regenerating gases.

The regenerating temperature is not particularly restricted as long as the catalyst is not thermally deteriorated at the temperature, but is preferably in the range from room temperature to the temperature which the reactor design endures, typically 300° C. or less, more preferably in the range of 20 to 200° C. The organic substances adhered are oxidized and decomposed by ozone, so that a temperature distribution typically occurs within the catalytic layer. In order to prevent thermal deterioration of the catalyst in the regenerating process, it is necessary to prevent the highest temperature of the catalytic layer from exceeding the range of the above-mentioned temperature.

When the catalyst is regenerated without discharging the catalyst from the adiabatic reactor, for instance the heat of oxidation reaction is absorbed by the sensible heat of the regenerating gas. One example of the regenerating process is given: the rate of the catalyst regeneration is high at the initial stage where a large amount of organic substance is deposited, so that the deposited organic substance is gradually reduced by keeping the temperature of the regenerating gas to be fed and the concentration of ozone at a low level. Conversely, the rate of the catalyst regeneration becomes low when the amount of the deposited organic substance became small. The temperature of the regenerating gas to be fed and the concentration of ozone are therefore gradually increased. At this time, the highest temperature of the catalytic layer must be kept not to be over the above-mentioned temperature. These conditions cannot be unambiguously defined because they depend on the amount of the deposited organic substance, the heat transfer coefficient and specific heat of the catalyst, the concentration of ozone and the amount of the regenerating gas. However, the conditions are preferably chosen from the above-mentioned range.

Examples of methods of contacting an inorganic solid catalyst with ozone in a gas phase include: a method of exposing the catalyst discharged from the reactor to an atmosphere of the ozone-containing gas, and a method of passing the ozone-containing gas through a fluidized-bed reactor or a fixed-bed reactor. The ozone processing can be carried out by discharging the deactivated catalyst from the reactor, but the operation thereof is very complex. Thus, it is preferable to perform the process in industrial operation without discharging the catalyst from the reactor. In this case, the ozone-containing gas is passed through the catalytic layer.

It is preferable to provide a rinsing process prior to the regenerating process. This is the process of flushing the alkanolamines, which are the product, in the reaction system outward, or the process of desorbing and removing the alkanolamines adsorbed in the catalyst. This process is performed by rinsing them with a liquid such as ammonia or carbon dioxide and/or a fluid under the sub critical or supercritical condition. Other solvents are optionally used.

The regeneration process of the invention may be performed after the amount of the deposited organic substance has been reduced by use of a drying process in a reduced condition, a rinsing process, and a pyrolysis process. The time for the regeneration can be thereby occasionally shortened.

Figure 6:
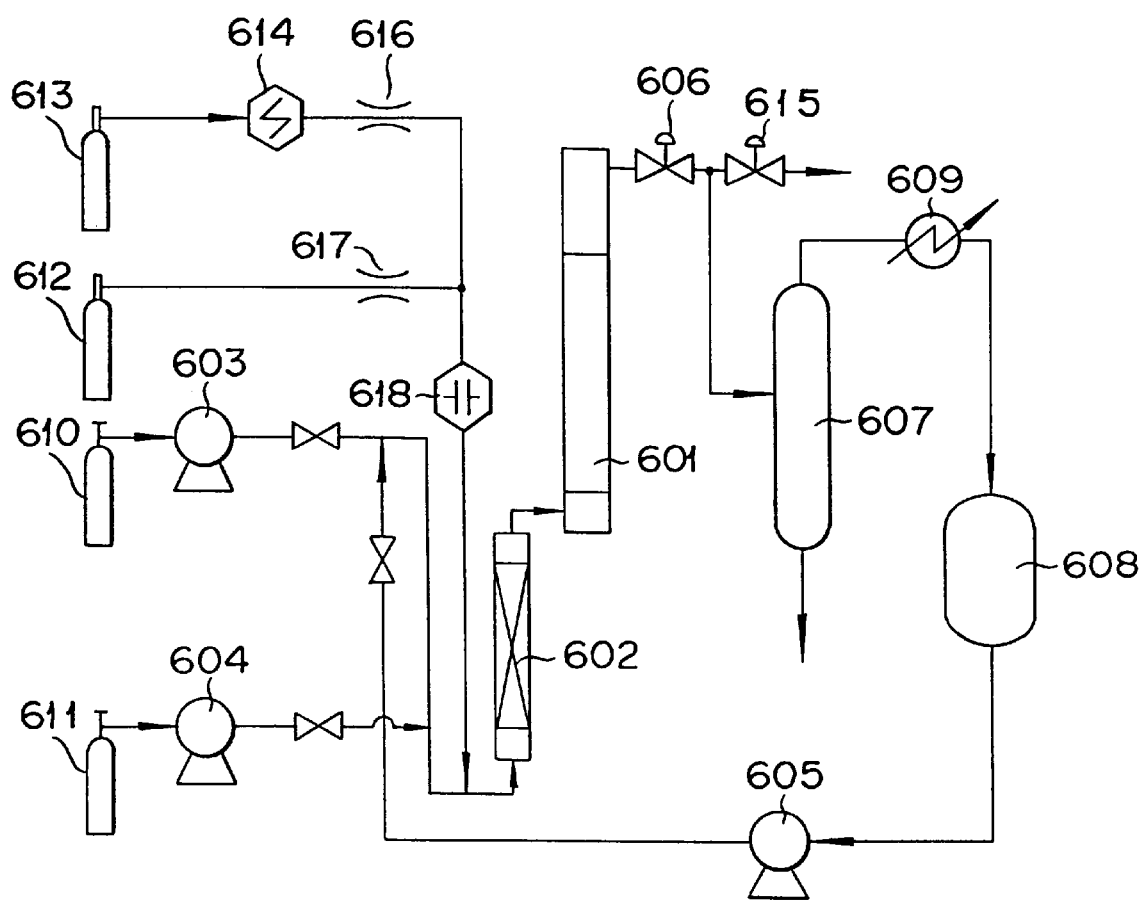
FIG. 6 is a schematic diagram of the reaction apparatus that was used in Example III.

A method of regenerating the catalyst of the invention will be described with reference to the drawing. FIG. 6 is a flowchart explaining a process of producing alkanolamines and a regenerating process of the catalyst. The process of producing the alkanolamines will be first described. In FIG. 6, ethylene oxide, which is one of alkylene oxides as a raw material, is fed in a predetermined amount from a tank for ethylene oxide 611 via a high-pressure pump 604 to a pre-heater 602, and at the same time ammonia is fed in a predetermined amount from a tank for ammonia raw 610 via a high-pressure pump 603 to the pre-heater 602. The pre-heated raw material mixture is fed to a reactor 601 in which the catalyst is filled, while adjusting the pressure by a pressure control valve 606, to carry out the reaction and produce the ethanolamines. The produced ethanolamines are introduced to an ammonia-flash tower 607, and collected as a bottom liquid, and the unreacted ammonia is distilled off from the tower top and condensed in a heat exchanger 609, to store the ammonia in an ammonia tank 608. The collected ammonia is reused as the raw material via a high-pressure pump 605.

The regenerating process of the catalyst will be described. When the reaction was ended, liquid ammonia (the pressure: 1–20 MPa) is pre-heated, if necessary, used to rinse the deactivated catalyst, and then discharged through an outlet valve 615 outward. After stopping the feed of the liquid ammonia, and reducing the pressure to atmospheric pressure by purging, the ozone-containing gas was fed (GHSV=200 h$^{-1}$). The ozone-containing gas is meant ozone generated by an ozone generator 614 is carried by pure oxygen gas from an oxygen gas tank 612. Further, the ozone-containing gas thus obtained is mixed with nitrogen gas from a nitrogen gas tank 612, and then the concentration of ozone is measured by an ozone analyzer 618, with the result that a flow volume is controlled by means of flow regulators 616 and 617 so as to adjust the concentration of ozone to a certain level. The ozone-containing gas is heated to a predetermined temperature with the pre-heater 602, and passed through the reactor 601, to regenerate the deactivated catalyst. The ozone-containing gas is discharged via the outlet valve 615 from the system.

It is possible to regenerate the deactivated catalyst efficiently without thermally deteriorate the catalyst by use of the ozone in a gas phase.

EXAMPLES

The present invention will be described in detail by way of examples, which should not be constructed as limiting the invention thereto.

The invention will be explained by the production of ethanolamines by use of chiefly ethylene oxide as an alkylene oxide.

REFERENCE EXAMPLE

Two (2) kg of zeolite ZSM-5 (the atomic ratio of Si/Al: 28/1, proton type, available from Zeolyst CO.) was placed in 10 liters of an aqueous solution containing lanthanum nitrate (1 mol/liter, 60° C.), and the mixture was subjected to ion exchange by keeping the mixture with stirring at 60° C. for 12 hrs. The mixture was filtrated, washed with water, and dried at 120° C. for 12 hrs. To the produced powder of the lanthanum-ion-exchanged ZSM-5 was added 700 g of clay, the resultant mixture was moisture-conditioned while being mixed with a kneader, and then molded with a dome-type die by use of a molding extruder into a string-like molded product having a diameter of 0.4 mm. The resultant molded product was dried at 120° C. for two hrs, prepared in the length range of 2–5 mm with a grain-size adjuster, and then dried at 120° C. for 12 hrs. The resultant molded product was calcined at 550° C. for three hrs in air. The calcined product is referred to as catalyst A.

Example 1-1

This example is a case where a regenerating process and a reaction process were repeated by use of a single reactor. The reaction was carried out by use of the apparatus shown in FIG. 4. A stainless steel tube having an inner diameter of 15 mm, a length of 400 mm, a heater wound thereon for compensating the heat radiation, and a heat-insulation was used as a reactor 401. Within the reactor, a protection tube where a thermocouple could be inserted to measure the temperature profile of a fixed catalytic layer was installed. Into the reactor was filled 50 ml of catalyst A, and the raw material (the molar ratio of ammonia/ethylene oxide: 14/1) heated to 60° C. via a pre-heater 402 was fed thereto at 5 hr$^{-1}$ (LHSV), to carry out the reaction.

Though the temperature increased up to 150° C. by the heat of reaction over the length of about 100 mm from the inlet at the initial stage, the temperature came to have a profile barely rising to nearly 150° C. after 500 hrs near the outlet of the catalytic layer. As a result, a reduction in the catalytic activity was observed.

The results obtained are as follows: the conversion of ethylene oxide was 100%; and the ratio of each component in the produced ethanolamines was: monoethanolamine/diethanolamine/trietanolamine=69/30/1. Diethanolamine was produced at a high selectivity though a small amount of triethanolamine was produced.

The deactivated catalyst was taken out of the reactor, heated in air up to 550° C. at a rate of 1° C. per minute, and then calcined again for three hrs. The regenerated catalyst was filled into the reactor in a similar manner, and the reaction was carried out. As a result, the catalyst showed the activity similar to the one at the initial stage, the distribution of the products did not change, and both the activity and the selectivity proved to have recovered.

Example 1-2

This example is a where a single reactor was used, and a regenerating process and a reaction process were repeated. The reaction was carried out by use of the apparatus shown in FIG. 4. A stainless steel tube having an inner diameter of 15 mm, a length of 400 mm, a heater wound thereon for compensating the heat radiation, and a heat-insulation was used as a reactor 401. Within the reactor, a protection tube where a thermocouple could be inserted to measure the temperature profile on a fixed catalytic layer was installed. Into the reactor was filled 50 ml of catalyst A, and the raw material (the molar ratio of ammonia/ethylene oxide: 14/1) heated to 60° C. via a pre-heater 402 was fed thereto at 5 hr$^{-1}$ (LHSV), to carry out the reaction.

Though the temperature increased up to 150° C. by the heat of reaction over the length of about 100 mm from the inlet at the initial stage, the temperature came to have a profile barely rising to nearly 150° C. after 500 hrs near the outlet of the catalytic layer. As a result, a reduction in the catalytic activity was observed.

The results obtained are as follows: the conversion of ethylene oxide was 100%; and the ratio of each component in the produced ethanolamines was: monoethanolamine/diethanolamine/trietanolamine=69/30/1. Diethanolamine was produced at a high selectivity while a small amount of triethanolamine was produced.

When the reaction was ended, liquid ammonia of 100° C. was fed at 5 hr$^{-1}$ (LHSV) for 30 minutes to rinse.

The deactivated catalyst was taken out of the reactor, heated in air up to 550° C. at a rate of 1° C. per minute, and further calcined again for three hrs. The regenerated catalyst was filled into the reactor in a similar manner, and the reaction was carried out. As a result, the catalyst showed the activity similar to the one at the initial stage, the distribution of the products did not change, and both the activity and the selectivity proved to have recovered.

Example II-1

The reaction was carried out by use of the apparatus shown in FIG. 5. A stainless steel tube having an inner diameter of 15 mm, a length of 400 mm, a heater wound thereon for compensating the heat radiation, and a heat-insulation was used as a reactor 501. Within the reactor 501, a protection tube where a thermocouple could be inserted to measure the temperature profile of a fixed catalytic layer, was installed. Into the reactor 501 was packed 50 cm$^3$ of catalyst A, and the raw material (the molar ratio of ammonia/ethylene oxide: 8/1) heated to 60° C. through a pre-heater 502 was fed at 5 hr$^{-1}$ (LHSV), to carry out the reaction. The reaction pressure was 10 MPa, and the reaction was in a gas-liquid mixing phase. Though the temperature increased up to 150° C. by the heat of reaction over the length of about 100 mm from the inlet at the initial stage, the temperature came to have a profile barely rising to nearly 150° C. after 200 hrs near the outlet of the catalytic layer. As a result, a reduction in catalytic activity was observed. The results obtained are as follows: the conversion of ethylene oxide was 100%; and the ratio of each component in the produced ethanolamines was: monoethanolamine/diethanolamine/trietanolamine=51/46/3. Diethanolamine was produced at a high selectivity while a small amount of triethanolamine was produced.

When the reaction was ended, liquid ammonia of 100° C. was fed at 5 hr$^{-1}$ (LHSV) for 10 minutes to rinse. The deactivated catalyst was taken out of the reactor for analysis, and a small part of this was washed with water for the analysis, and was subjected to elemental analysis of the organic substance that adhered to the catalyst. The analytical results obtained are as follows: carbon 6.4% by weight, hydrogen 1.6% by weight, and nitrogen 1.3% by weight.

This catalyst was filled to the reactor again, further the pressure of the reactor was controlled at 15 MPa, the temperature of the pre-heater was increased up to 180° C., and liquid ammonia was fed to the reactor at 5 hr$^{-1}$ (LHSV) to carry out a first regeneration. The regenerating process was performed for 50 hrs, the resultant regenerated catalyst was taken out of the reactor. Part of the regenerated catalyst, which was not washed with water, was subjected in a similar manner to elemental analysis of the organic substance, which remains in the catalyst. The analytical results obtained are as follows: carbon 0.88% by weight, hydrogen 0.71% by weight, and nitrogen 2.18% by weight. It is understood that the nitrogen originates from the adsorbed ammonia, and the organic substance deposited had been almost removed.

Further, this catalyst was filled to the reactor, and then the reaction was carried out under the same conditions as in the initial reaction. It is understood that the temperature distribution of the catalytic layer at the initial stage, after the regeneration, became about 150° C. over the length of about 150 mm from the inlet, and that the activity had considerably recovered. The reaction was continued for 200 hrs as it was, and when a reduction in the catalytic activity began, the second regeneration was carried out by use of the treatment using ammonia under the same conditions as in the first regeneration. By this treatment the activity had recovered in the same level as after the first regeneration.

Example II-2

The reaction was repeated under the same conditions as in Example II-1, and the regenerating process was carried out under the same conditions except that the processing temperature was 200° C. The temperature distribution of the catalytic layer at the initial stage of the reaction following the regeneration was about 150° C. over the length of 130 mm from the inlet. As a result, an activity of the regenerated catalyst had considerably recovered.

Example II-3

The reaction was repeated under the same conditions as in Example II-1, and the regenerating process was carried out under the same conditions except that the processing pressure was 10 MPa. The temperature distribution of the catalytic layer at the initial stage of the reaction following the regeneration was about 150° C. over the length of 130 mm from the inlet. As a result, an activity of the regenerated catalyst had considerably recovered.

Example II-4

The reaction was repeated under the same conditions as in Example II-1, and the regenerating process was carried out under the same conditions as in Example II-3 except that the processing temperature was 230° C., and the processing time was 24 hrs. A part of the regenerated catalyst was taken out, and was, without washing it with water, subjected to elemental analysis of the organic substance adhering to the catalyst. The analytical results obtained are as follows: carbon 0.37% by weight, hydrogen 0.64% by weight, and nitrogen 1.43% by weight. It is understood that the nitrogen originates from the adsorbed ammonia, and the organic substance adhering to the catalyst had been almost removed.

The temperature distribution of the catalytic layer at the initial stage of the reaction following the regeneration was about 150° C. over the length of 130 mm from the inlet. As a result, an activity of the regenerated catalyst had considerably recovered.

Example II-5

The reaction was performed under the same conditions as in Example II-1. The regenerating process was performed under the same conditions as in Example II-4, and the amounts of the high-boiling-point organic substances such as triethanolamine or the like in the collected ammonia were analyzed quantitatively by gas chromatography. As a result, the amounts of the high-boiling-point organic substances proved to decrease with time, and reach the lower limit of detection of 50 ppm or less after 24 hrs from the initiation of the regeneration.

The temperature distribution of the catalytic layer at the initial stage of the reaction using the regenerated catalyst was about 150° C. over the length of 130 mm from the inlet. As a result, an activity of the regenerated catalyst had been considerably recovered.

Subsequently, the reaction was performed under the same conditions as in Example II-1, and the regenerating process was repeated 10 times under the same conditions as in Example II-4. A change in the temperature distribution of the catalytic layer was not found at each initial stage of the reaction subsequent to the regeneration performed 2–10 times, so that the deterioration of the catalyst caused by the repetition of the regeneration was not recognized Comparative Example II-1

The reaction was performed under the same conditions as in Example II-1. When the reaction was ended, the reactor was rinsed with liquid ammonia, and then the ammonia was purged from the system. A nitrogen gas heated to 200° C. was passed through the reactor at 200 hr$^{-1}$ (SV) for 72 hrs. When the treated catalyst was discharged, the color thereof was found to become gray. The elemental analysis of the organic substance adhering to the catalyst was performed. The analytical results obtained are as follows: carbon 6.3% by weight, hydrogen 1.5% by weight, and nitrogen 1.2% by weight. These values changed little compared with the ones prior to the regeneration process. The removal of the organic substance from the catalyst could not be achieved.

Comparative Example II-2

The reaction was repeated under the same conditions as in Example II-1. When the reaction was ended, the reactor was rinsed with liquid ammonia. An ammonia gas heated to 200° C. was passed through the reactor at atmospheric pressure at 200 hr$^{-1}$ (SV) for 72 hrs. When the treated catalyst was discharged, the color thereof was found to slightly become gray. The elemental analysis of the organic substance adhering to the catalyst was performed. The analytical results obtained are as follows: carbon 5.3% by weight, hydrogen 1.7% by weight, and nitrogen 1.6% by weight. The amount of the organic substance decreased, but the rate was small. The removal of the organic substance from the catalyst could not be sufficiently achieved.

Example III-1

The reaction was carried out by use of an apparatus shown in FIG. 6. A stainless steel straight tube having an inner diameter of 40 mm, a length of 80 mm, a heater wound thereon for compensating the heat radiation, and a heat-insulation was used as a reactor 601. Within the reactor, a protection tube where a thermocouple could be inserted to measure the temperature profile of the catalytic layer was installed. Into the reactor was packed 50 ml of catalyst A, and the raw material (the molar ratio of ammonia/ethylene oxide: 14/1) heated to 60° C. via a pre-heater 602 was fed at 5 hr$^{-1}$ (LHSV), to carry out the reaction.

Though the temperature increased up to 150° C. by the heat of reaction over the length of about 20 mm from the inlet at the initial stage, the temperature came to have a profile barely rising to nearly 150° C. after 500 hrs near the outlet of the catalytic layer. As a result, deterioration in catalytic activity was observed. The results obtained are as follows: the conversion of ethylene oxide was 100%; and the ratio of each component in the produced ethanolamines was: monoethanolamine/diethanolamine/triethanolamine=69/30/1. Diethanolamine was produced at a high selectivity while a small amount of triethanolamine was produced.

When the reaction was ended, liquid ammonia was fed at 5 $hr^{-1}$ (LHSV), to replace the inner atmosphere of the reactor.

The feed of liquid ammonia was stopped, the pressure therein was reduced to atmospheric pressure by a purge, and then an ozone-containing gas was fed (GHSV=200 $hr^{-1}$) thereto under the conditions described in Table 1, to regenerate the catalyst. The highest temperature of the catalyst (the maximum value) was 148° C. in the regeneration. A part of the regenerated catalyst was taken out to perform the elemental analysis for the organic substance deposited on the catalyst. The analytical results obtained are as follows: carbon 0.1% by weight, hydrogen 0.5% by weight, and nitrogen 0.15% by weight.

When the reaction was carried out in a similar manner after the regeneration, it was found that the catalyst showed the activity similar to the one at the initial stage, no change in the distribution of the product occurred, and both the activity and the selectivity had recovered.

Example III-2

The reaction was performed under the same conditions as in Example III-1 for 500 hrs.

When the reaction was ended, liquid ammonia was fed at 5 $hr^{-1}$ (LHSV) for 30 minutes, to replace the inner atmosphere of the reaction pipe.

The feed of liquid ammonia was stopped, the pressure therein was reduced to atmospheric pressure by a purge, and an ozone-containing gas was fed (GHSV=400 $hr^{-1}$) thereto under the conditions described in Table 1, to regenerate the catalyst. The highest temperature of the catalyst (the maximum value) was 176° C. in the regeneration. A part of the regenerated catalyst was taken out to do the elemental analysis of the organic substance deposited on the catalyst. The analytical results obtained are as follows: carbon 0.07% by weight, hydrogen 0.1% by weight, and nitrogen 0.07% by weight.

When the reaction was carried out in a similar manner after the regeneration, it was found that the catalyst showed the activity similar to the one at the initial stage, no change in the distribution of the product occurred, and both the activity and the selectivity had recovered.

TABLE 1

|  | Regeneration time (hr) | Temperature for pre-heater (° C.) | Concentration of ozone (% by volume)* |
|---|---|---|---|
| Example III-1 | 0–90 | 40 | 0.4 |
|  | 90–150 | 50 | 0.5 |
|  | 150–200 | 80 | 0.5 |
|  | 200–250 | 100 | 0.6 |
|  | 250–300 | 100 | 1.0 |
| Example III-2 | 0–60 | 50 | 0.3 |
|  | 60–80 | 70 | 0.5 |
|  | 80–100 | 100 | 0.5 |

TABLE 1-continued

| Regeneration time (hr) | Temperature for pre-heater (° C.) | Concentration of ozone (% by volume)* |
|---|---|---|
| 100–120 | 100 | 0.75 |
| 120–150 | 120 | 1.0 |

*Balanced gas = nitrogen

Comparative Example III-1

The reaction was repeated under the same conditions as in Example III-1 for 500 hrs.

When the reaction was ended, liquid ammonia was fed at 5 $hr^{-1}$ (LHSV) for 30 minutes, to replace the inner atmosphere of the reactor.

The deactivated catalyst was taken out, and washed with water, to do the elemental analysis of the organic substance adhering to the catalyst. The analytical results obtained are as follows: carbon 6.5% by weight, hydrogen 1.6% by weight, and nitrogen 1.3% by weight.

The entire disclosure of Japanese Patent Application Nos. 11-336028, 2000-138785, 2000-166882 filed on Nov. 26, 1999, May 11, 2000 and Jun. 5, 2000, respectively, including specification, claims, drawings and summary are incorporated herein by reference in its entirety.

What is claimed is:

1. A method of producing an alkanolamine, which comprises alternatively repeating the following two processes:
    a reaction process for reacting ammonia with an alkylene oxide in the presence of a microporous material catalyst; and
    a regenerating process for regenerating a deactivated catalyst;
    wherein the regenerating process is performed by passing ammonia through the deactivated catalyst in the range of 100 to 350° C.

2. A method according to claim 1, wherein at least two reactors are prepared, the regeneration process is performed in at least one of the reactors, while the reaction process is performed in the remaining reactor.

3. A method according to claim 1, wherein the reaction is carried out by connecting in series a part or all of the multiple reactors used in the reaction process, separating the reactor including the most deactivated catalyst from the reaction process successively to switch it to the regenerating process, and switching the regenerated reactor to the reaction process.

4. A method according to claim 1, wherein the regenerating process is performed in the pressure of 1 to 30 MPa.

5. A method according to claim 1, wherein the alkylene oxide is at least one member selected from the group consisting of ethylene oxide and propylene oxide.

6. A method according to claim 1, wherein the reactor is a fixed bed reactor.

7. A method according to claim 1, wherein the reaction process is performed in a liquid phase.

8. A method according to claim 1, wherein the ammonia has substantially no water.

9. A method according to claim 1 further comprising determining a reduction of the catalyst activity based on the temperature distribution between an inlet to the catalyst and an outlet from the catalyst.

10. A method according to claim 1 further comprising determining a degree of the regeneration of the catalyst based on an amount of an organic substance remaining on or within the catalyst.

11. A method according to claim 1 further comprising determining a degree of the regeneration of the catalyst based on an amount of high boiling materials in the ammonia that has passed through the catalyst.

* * * * *